Figure 1:
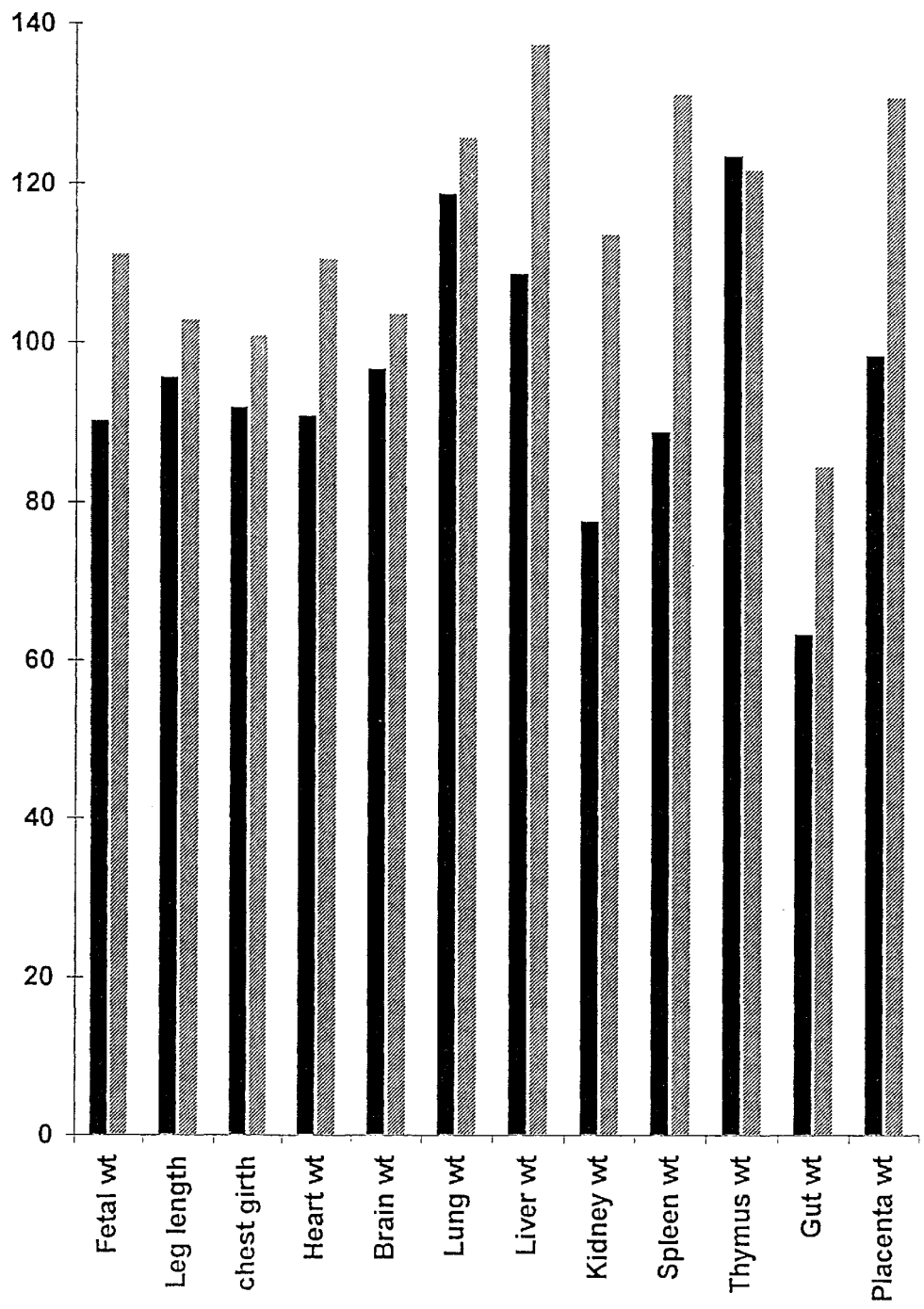

United States Patent [19]

Harding et al.

[11] Patent Number: 5,858,966

[45] Date of Patent: Jan. 12, 1999

[54] FETAL GROWTH

[75] Inventors: Jane Elizabeth Harding; Roy Mark Kimble; Peter David Gluckman, all of Auckland, New Zealand

[73] Assignee: Auckland UniServices Limited, Auckland, New Zealand

[21] Appl. No.: 849,474

[22] PCT Filed: Dec. 19, 1995

[86] PCT No.: PCT/NZ95/00132

§ 371 Date: Jun. 10, 1997

§ 102(e) Date: Jun. 10, 1997

[87] PCT Pub. No.: WO96/19235

PCT Pub. Date: Jun. 27, 1996

[30] Foreign Application Priority Data

Dec. 21, 1994 [NZ] New Zealand .......................... 270239

[51] Int. Cl.$^6$ ..................................................... A61K 38/28

[52] U.S. Cl. ..................................................... 514/3; 514/3

[58] Field of Search ................................ 514/21; 530/303, 530/399, 324

[56] References Cited

U.S. PATENT DOCUMENTS 5,420,111  5/1995  Gluckman et al. ....................... 574/12

OTHER PUBLICATIONS

Harding et al., Eudocrinology, vol. 134, No. 3, pp. 1509–1514.
Liu et al., Endocrinology, vol. 124, No. 6, pp. 3077–3082.

*Primary Examiner*—Cecilia J. Tsang
*Assistant Examiner*—C. Delacroix-Muirheid
*Attorney, Agent, or Firm*—Young & Thompson

[57] ABSTRACT

A method of enhancing fetal growth and/or development and/or neonatal survival by the administration over a period of insulin-like growth factor (IGF-1), to either the amniotic fluid or direct to the fetal gastrointestinal tract. Administration may be by way of an ultrasonically monitored injection or placement of a catheter.

8 Claims, 1 Drawing Sheet

FETAL GROWTH

FIELD OF THE INVENTION

This invention relates to the treatment of mammalian fetuses (including human fetuses) with compositions that enhance the ability of the fetus and neonatal infant to survive.

BACKGROUND

Intrauterine growth retardation (IUGR) remains a major cause of intrauterine and neonatal death and is associated with a high morbidity in the neonatal period and potentially with morbidity extending to adult life. It is frequently associated with abnormalities of placental growth and/or function. IUGR can be diagnosed with standard obstetrical techniques such as ultrasonography. However treatment of IUGR remains inadequate and restricted to either maternal bedrest or premature elective caesarean section.

Immaturity of lung growth and development in fetal life may occur associated with IUGR or independent of it. Isolated failure of fetal lung growth is known as pulmonary hypoplasia and is a significant cause of neonatal death. It may be diagnosed prenatally. In prematurely born infants, immaturity of lung structure and function leads to the respiratory distress syndrome (RDS). RDS is currently treated by ventilation and pulmonary insufflation of surfactant but remains a major problem in neonatal nurseries. It has been the practice for many years to treat women at risk of premature birth or in premature labour, where delivery is delayed pharmaceutically, with steroid hormones which cross the placenta and mature the lungs. However this therapy only partially alleviates RDS.

It is known to those versed in the art that fetal growth is regulated in part by a hormone termed insulin-like growth factor-1 (IGF-1) which circulates in the fetal circulation and which has been demonstrated in a variety of animal models to regulate fetal growth and confirming clinical data are available. IGF-1 is made by fetal tissues. It however does not cross the placenta from mother to fetus. Therefore maternal administration does not directly affect fetal circulating levels of IGF-1 and that maternal administration of IGF-1 affects fetal growth indirectly (Liu L, Harding J E, Evans P C, Gluckman P D. "Maternal IGF-1 alters feto-placental carbohydrate and protein metabolism in pregnant sheep". Endocrinology 135 895–900; 1994). IGF-1 in the fetal circulation is derived from fetal tissues in particular from the fetal liver.

It is also known that the fetus swallows amniotic fluid.

OBJECT

It is an object of the present invention to provide an improved composition and/or method for treating intrauterine growth retardation or one which will at least provide the public with a useful choice.

STATEMENT OF THE INVENTION

In a first broad aspect the invention provides method of enhancing growth and/or maturation of a fetus and/or its immune system and/or its organs characterised in that IGF-1 is administered to amniotic fluid or to the gastrointestinal tract of the fetus.

Preferably the IGF-1 is administered to the amniotic fluid to promote placental growth.

More preferably the IGF-1 is administered to the amniotic fluid by a single or repeated amniocentesis injection.

Alternatively the IGF-1 is administered to the amniotic fluid by placement of a chronic cannula.

Alternatively the IGF-1 is administered into the fetal gastrointestinal tract by injection or placement of a catheter.

Preferably IGF-1 is chosen from the group comprising recombinant human IGF-1, or the recombinant form of its naturally occurring analogue des 1–3N IGF-1.

Preferably the IGF-1 is administered together with recombinant forms of its binding protein.

Preferably the dose of IGF-1 administered per day is in the range of 1–100 $\mu$g/kg estimated fetal weight.

In another aspect the invention provides a composition for enhancing fetal growth comprising an effective amount of IGF-1 and a pharmaceutically acceptable carrier.

In another aspect the invention is concerned with the use of IGF-1 in the manufacture of a composition to enhance fetal growth.

The IGF-1 can be administered into amniotic fluid surrounding the fetus or to the gastrointestinal tract of the fetus to enhance growth or maturation of the placenta or growth or maturation of various organs or organ systems of the fetus which lead to enhanced neonatal survival, eg the fetal lungs, or the fetal immune system.

Alternatively the invention comprises a method for treatment as described above, in which precursors of IGF-1 or compounds capable of stimulating its synthesis are administered to a pregnant female animal—including a human female.

In a related aspect the cannula for the fetal gastrointestinal tract may be positioned with the aid of ultrasonic monitoring.

In a further related aspect the IGF-1 may be injected in aqueous form or in a slow-release gel or pellet or in combination with an adjuvant which provides for slow release.

In a yet further related aspect the invention comprises a method for treatment as described above, in which precursors of IGF-1 or compounds capable of stimulating its synthesis are administered.

In a yet further related aspect the invention comprises a mode of treatment as described in this section, in which the dose rate of IGF-1 corresponds to between one and one hundred micrograms per kilogram estimated fetal weight per day.

DRAWINGS

The following is a description of a preferred form of the invention, given by way of example only, with reference to the accompanying diagram.

FIG. 1: is a graphical illustration of effects of IGF-1.

PREFERRED EMBODIMENT

Prior to this disclosure it was not known that IGF-1 in the amniotic fluid contributed to fetal development. The essence of this invention is that we have found that infusion of IGF-1 into the fetal gastro-intestinal system in amounts comparable to those that could be achieved by administration into the amniotic fluid and subsequent fetal ingestion enhances fetal growth, and promotes the growth of fetal organs including the lung and immune system.

EXAMPLE 1.

Fetal sheep of known gestational age (term gestation 147 days) were subject to surgery at 90 days. Three groups of animal were studied. One group served as a normal comparative group and the other two groups were operated on. In both operated groups the oesophagus was ligated and the upper limb of the cut oesophagus marsupialised to the fetal neck so that fetal swallowing movements were not disturbed, but swallowed fluid simply returned to the amniotic space without entering the fetal stomach. A catheter was placed in the fetal gastrointestinal system distal to the ligation. Into this catheter was infused recombinant human IGF-1 (courtesy of Dr L Fryklund, Pharmacia AB, Stockholm) dissolved in saline. The amount of IGF-1 infused was initially 2 μg daily increasing with gestational age to 8 μg/day which was estimated to be twice the amount that the fetus would normally swallow from amniotic fluid. A third group of animals had a similar operation but saline only was infused at 1 ml/hr. This rate is about 1% of the normal rate of fluid swallowed per day by the fetus.

The infusion was continued until 137 days, when the ewe was sacrificed and fetal and placental sizes were measured.

|  | Normal | Saline | IGF-1 |
|---|---|---|---|
| No. animals | 4 | 5 | 4 |
| Fetal weight (gm) | 4021 | 3633 | 4472 |
| Leg length (cm) | 35 | 33.5 | 36 |
| Chest girth (cm) | 35.9 | 33 | 36.2 |
| Heart weight (gm) | 29.5 | 26.8 | 32.6 |
| Brain weight (gm) | 48.5 | 46.9 | 50.2 |
| Lung weight (gm) | 98.7 | 117.1 | 124 |
| Liver weight (gm) | 110 | 119.4 | 151 |
| Kidney weight (gm) | 31.3 | 24.1 | 35.3 |
| Spleen weight (gm) | 7.1 | 6.3 | 9.3 |
| Thymus weight (gm) | 11.6 | 14.3 | 14.1 |
| Gut weight (gm) | 161 | 102 | 136 |
| Placental weight (gm) | 287 | 282 | 375 |

(Normal" means the normal comparative group, "saline" means those infused with saline, and "IGF-1" means those infused with IGF-1 as described herein. FIG. 1 illustrates these FIGURES in graphical form, with the vertical column representing percentage. Each solid black column represents the saline-treated fetus results as a percentage of the corresponding control results, and each hatched or shaded column represents the IGF-1 treated fetus results as a percentage of the corresponding control results.

It can be seen that relative to normal animals, those fetuses where amniotic fluid does not reach the stomach are growth-retarded. In contrast, those fetuses treated with intraluminal IGF-1 are larger than either normal or control animals. Relative to body weight they show disproportionate growth of the liver, lungs and immune system.

It is apparent from these results that IGF-1 in amniotic fluid can affect fetal growth and specifically enhance the growth of some organs such as the lung. Furthermore it is apparent that increasing the intraluminal exposure to IGF-1 by IGF-1 infusion enhances growth relative to the other groups and can further increase lung growth.

This result is surprising in that intraluminal IGF-1 postnatally has no such effects on overall growth and development other than specific effects restricted to the gastrointestinal system. Young et al Digestion 46 (1990) Supplement 2, 240–252 discloses effects of intraluminal IGF-1 in infant rats as being restricted to effects on jejunal enzymes only. Gluckman et al (PCT/SE93/00502)disclose that oral IGF-1 in neonatal piglets affects pancreatic growth only. Thus there was no a priori reason to believe that intraluminal IGF-1 in utero could affect systemic growth.

We therefore propose that enhancing the IGF-1 concentrations either in amniotic fluid or in the fetal gastrointestinal tract is a way of promoting fetal growth in the fetus with IUGR. There may be ways to enhance its autogenous production, either by providing precursors or by providing specific stimulants to IGF-1 production. It may also be a way of enhancing the growth and maturation of organs such as the lung in those fetuses destined to be born with small or immature lungs, or with dysmaturity of the immune system, or gastrointestinal system, as is also observed in immature premature babies.

Finally, it will be appreciated that various alterations and modifications may be made to the foregoing without departing from the scope of this invention as set forth.

We claim:

1. A method of enhancing growth of a fetus or its organs, comprising administering IGF-1 to amniotic fluid or to the gastrointestinal tract of the fetus.

2. A method as claimed in claim 1 wherein the IGF-1 is administered to the amniotic fluid to promote placental growth.

3. A method as claimed in claim 1 wherein the IGF-1 is administered to the amniotic fluid by a single or repeated amniocentesis injection.

4. A method as claimed in claim 1 wherein the IGF-1 is administered to the amniotic fluid by placement of a chronic cannula.

5. A method as claimed in claim 1 wherein the IGF-1 is administered into the fetal gastrointestinal tract by injection or placement of a catheter.

6. A method as claimed in claim 1, wherein the IGF-1 is selected from the group consisting of recombinant human IGF-1 and recombinant form of its naturally occurring analogue des 1–3 N IGF-1.

7. A method as claimed in claim 1 wherein the IGF-1 is administered together with recombinant forms of its binding protein.

8. A method as claimed in claim 1 where the dose of IGF-1 administered per day is in the range of 1–100 μg/kg estimated fetal weight.

* * * * *